United States Patent [19]

Metzger

[11] 4,185,092

[45] Jan. 22, 1980

[54] PURIFICATION OF NYSTATIN IN AN AQUEOUS SYSTEM

[75] Inventor: Julio Metzger, Humacao, P.R.

[73] Assignee: E. R. Squibb & Sons, Inc., Princeton, N.J.

[21] Appl. No.: 839,075

[22] Filed: Oct. 3, 1977

[51] Int. Cl.$^2$ ............................................. A61K 35/00
[52] U.S. Cl. ................................................. 424/123
[58] Field of Search ......................................... 424/123

[56] References Cited

U.S. PATENT DOCUMENTS

| | | | |
|---|---|---|---|
| 3,332,844 | 7/1967 | Vandeputte et al. | 424/123 |
| 4,006,222 | 2/1977 | Metzger | 424/123 |

FOREIGN PATENT DOCUMENTS 809105 2/1959 United Kingdom ..................... 424/123

*Primary Examiner*—Jerome D. Goldberg
*Attorney, Agent, or Firm*—Lawrence S. Levinson; Donald J. Barrack

[57] ABSTRACT

Crude, partially purified or contaminated nystatin is purified by suspending the nystatin starting material in water; extracting its activity with sodium lauryl sulfate; adding a chlorinated hydrocarbon solvent; and adding an acid-addition salt of an amine to yield an amorphous precipitate of the nystatin.

6 Claims, No Drawings

PURIFICATION OF NYSTATIN IN AN AQUEOUS SYSTEM

BACKGROUND OF THE INVENTION

The present invention relates to the antibiotic nystatin (referred to in the older literature as fungicidin), and more specifically to a process for the purification of crude, partially purified or contaminated nystatin.

Nystatin and its method of preparation from *Streptomyces noursei* are disclosed by Hazen et al. in U.S. Pat. No. 2,797,183. Reference may also be made to Hazen and Brown, "Fungicidin, An Antibiotic Produced by a Soil Actinomycete," Proc. Soc. Exptl. Biol. Med. 76:93 (1950) and Brown, Hazen and Mason, "Effect of Fungicidin (nystatin) in Mice Injected with Lethal Mixtures of Aureomycin and *Candida albicans,*" Science 117:609 (1953). The antibiotic is hereinafter referred to by the single term "nystatin".

Several methods for isolating nystatin from the fermentation media are known to the prior art. Examples of such processes are Hazen et al., U.S. Pat. Nos. 2,797,183; Vandeputte et al., 2,786,781; Vandeputte et al., 3,332,844; and Renella, 3,517,100. The nystatin isolated by known processes is not a highly purified, uniformly crystalline product. A method for obtaining nystatin in such a form is of course highly desirable, and several methods for achieving this result have been suggested by the prior art. For examples of such processes, reference may be made to Vandeputte, U.S. Pat. Nos. 2,832,719; Dutcher et al., 2,865,807; Mendelsohn, 3,509,255; Esse, 3,517,101; Keseleski et al., 3,911,113; and Metzger, 4,006,222.

British Pat. No. 809,105 deals with a process for water solubilizing amorphous nystatin, which comprises mixing the nystatin with an anionic surfactant, sodium lauryl sulfate being the most preferred.

U.S. Pat. No. 3,332,844 deals with a process for recovering nystatin from the fermentation broth in which it is produced. The process comprises extracting the wet mycelium in a medium comprising a lower alkanol, a mineral acid and an amine (the amine, which is preferably a tertiary amine, and the acid are preferably added together in the form of an acid-addition salt of the amine).

U.S. Pat. No. 4,006,222 deals with a process for the purification of nystatin in a lower alkanol system. The nystatin starting material is purified by first suspending it in a lower alkanol, solubilizing the nystatin with a weak organic acid, filtering off the lower alkanol extract, combining a chlorinated hydrocarbon solvent and the lower alkanol extract, neutralizing the resultant mixture, and precipitating purified nystatin by the addition of water.

BRIEF DESCRIPTION OF THE INVENTION

It is an object of this invention to provide a process for the purification of crude, partially purified or contaminated nystatin.

It is an object of this invention to provide a process for the purification of nystatin that will yield a product of high potency.

It is an object of this invention to provide a process that yields a highly purified nystatin product which can be readily converted into a crystalline form from a largely aqueous system.

These, and other objects that will be readily apparent from the description of the invention, are realized by the process of this invention. The process comprises:

(i) forming an aqueous solution of nystatin by combining the nystatin starting material with water and an anionic surfactant;

(ii) combining a chlorinated hydrocarbon solvent with the aqueous nystatin solution; and (iii) precipitating purified amorphous nystatin by adding an acid-addition salt of a mineral acid and a water-soluble amine.

DETAILED DESCRIPTION OF THE INVENTION

The nystatin employed as the starting material in the novel purification process of this invention can be crude, partially purified, or contaminated, substantially non-crystalline nystatin. The expression "contaminated nystatin" encompasses not only nystatin that contains chemical contaminants, but also nystatin contaminated with physical contaminants such as dirt particles, fibrous material, and other particulate elements that might cause nystatin to be unacceptable for pharmaceutical utility.

The nystatin starting material is first suspended in water. The amount of water used will be goverened by the potency of the resulting nystatin suspension, which should be at least about 5000 $\mu$g/ml, and preferably be at least 10,000 $\mu$g/ml. The nystatin is then solubilized with an anionic surfactant, preferably sodium lauryl sulfate. The amount of surfactant needed to solubilize the nystatin will depend on several factors, including the physical characteristics of the nystatin starting material and the concentration of nystatin in suspension. Generally, however, the weight ratio of nystatin to sodium lauryl sulfate will be from about 1:2 to 1:6, preferably from about 1:3 to 1:4.

Instead of adding sodium lauryl sulfate to an aqueous suspension of nystatin, as described above, it is also possible to first form an aqueous solution of sodium lauryl sulfate and then add the nystatin starting material to this solution.

The aqueous solution of nystatin prepared by either of the procedures described above should, if necessary, be filtered. This filtration step will, of course, be necessary if the nystatin starting material is contaminated. It may also be necessary in other instances, and this will be determined by observing whether or not the aqueous nystatin solution is clear. If it is not, filtration is desirable. To improve the efficiency of the filtration process, a filter aid, e.g., diatomaceous silica, may be added to the nystatin solution.

A chlorinated hydrocarbon solvent is added to the nystatin solution. Exemplary solvents are chloroform, dichloromethane, and others. For reasons of safety, dichloromethane is the preferred solvent. The amount of chlorinated hydrocarbon solvent added to the nystatin solution is based on the activity of nystatin in solution. An amount of about 0.6 to 1.4ml of chlorinated hydrocarbon solvent is used per million units of nystatin activity.

Precipitation of the nystatin from solution can be accomplished by the addition to the solution of an acid-addition salt of a mineral acid and water-soluble amine. While not preferred, it is possible to add a mineral acid and an amine instead of the amine salt.

The precipitate is a mixture of purified amorphous nystatin and an amine salt of the surfactant. The purified amorphous nystatin product can be separated out and converted to a crystalline product using known technology. For example, the mixture of amorphous nystatin and amine salt of the surfactant can be filtered (to remove water) and then slurried in a halogenated hydrocarbon solvent to dissolve the amine salt. Refiltering the product, rewashing it with a halogenated hydrocarbon solvent, and vacuum drying it at about 40–60° C, yields a crystalline product. Alternatively, nystatin seed crystals can be first added to the purified amorphous precipitate, prepared as described above, and the resulting slurry heated to about 40–60° C. Filtering, washing and vacuum drying can then be carried out as described above.

The following examples further illustrate this invention.

EXAMPLE 1

Nystatin (2.0g, chemical potency 5000 units/mg) is dissolved with about 15 minutes agitation in 200 ml of a 3% w/v aqueous sodium lauryl sulfate solution (20.8 mEq of sodium lauryl sulfate). The rich clear solution is transferred to a 500 ml round bottom flask equipped with an agitator and condenser. Dichloromethane (8.0 ml) is added followed by the slow addition (15 minutes) of 20 ml of a 1.04 molar aqueous solution of t-octylamine, hydrochloride (20.8 mEq t-octylamine, hydrochloride to give an amorphous milky precipitate.

Nystatin seed crystals (20 mg) are added and the slurry is warmed to 50° C. in about 15 minutes to initiate crystallization. The slurry is cooled to 25° C. over about 2 hours, and agitated for an additional hour. The mixture of nystatin and t-octylamine lauryl sulfate is filtered as dry as possible and slurried for 10 minutes in 30 ml of dichloromethane to dissolve the gelatinous t-octylamine derivative. The product is then refiltered, washed by displacement with two 10 ml portions of dichloromethane and vacuum dried for about 16–24 hours at 50° C. to give 1.56 g of nystatin product.

Yield is calculated to be 86.6% based on a product chemical potency of 5549 units/mg.

EXAPLE 2

Nystatin (2.0g, chemical potency of 5000 units/mg) is dissolved with about 12 minutes agitation in 200 ml of a 3% w/v aqueous sodium lauryl sulfate solution (20.8 mEq of sodium lauryl sulfate). To the clear solution in a 500 ml round bottom flask, equipped with an agitator and condenser is added 10.0 ml of dichloromethane, followed by the slow addition (8 minutes) of 20 ml of distilled water containing 5.68 g of procaine hydrochloride (20.8 mEq) to give a milky precipitate.

Nystatin seed crystals (20 mg) are added and the slurry is warmed to 50° C. The slurry is then gradually cooled to 10° C. (complete crystallinity occurs at 40° C.), agitated an additional hour at 10° C., filtered and displaced with acetone. The product (mixture of nystatin and procaine lauryl sulfate) is slurried for 10 minutes in 50 ml of dichloromethane, refiltered and washed by displacement with dichloromethane. Vacuum drying for 16–24 hours at 50° C. gives 1.54 g of nystatin product.

Yield is calculated to be 86.0% based on a product chemical potency of 5584 units/mg.

EXAMPLE 3

Nystatin, (2.0g representing 10 million units) is dissolved with about 15 minutes agitation in 200 ml of 3% w/v aqueous sodium lauryl sulfate solution (20.8 mEq of sodium lauryl sulfate). To the rich clear solution is added 10 ml of dichloromethane followed by the slow addition of 14.24 ml of (20.8 mEq) to give a milky precipitate.

Nystatin seed crystals (20 mg) are added to the slurry is warmed to 50° C., cooled gradually to 10° C., slurried one hour at 10° C., and filtered. The gelatinous cake is slurried for 15 minutes in 100 ml butanol, filtered and displacement washed with butanol. Vacuum drying for 16–24 hours at 50° C. gives 1.425 g of final product.

Yield is calculated to be 80.3% based on a product chemical potency of 5636 units/mg.

EXAMPLE 4

Crude intermediate nystatin (2.62 g, chemical potency of 3819 units/mg) is dissolved with about 10 minutes' agitation in 200 ml of a 3% w/v aqueous sodium lauryl sulfate solution. The resultant hazy solution is filtered after the addition of 1.0 g of diatomaceous earth. The clear solution is transferred to a 500 ml 3-neck round bottom flask equipped with an agitator and condenser. Dichloromethane (10 ml) is added, followed by the slow addition of 20 ml of a 10.4 molar aqueous t-octylamine hydrochloride solution, giving a milky precipitate.

Nystatin seed crystals (20 mg) are added and the slurry is warmed to 50° C. in about 20 minutes time. After cooling to room temperature over 2 hours and slurrying for an additional hour, crystalline nystatin material is observed. The wet cake is filtered, dried as much as possible on the filter, slurried for 10 minutes in 30 ml of dichloromethane, filtered and displaced with two 30 ml portions of dichloromethane. The product is then vacuum dried for 20 hours at 50° C.

Yield is calculated to be 77% based on a product chemical potency of 5766 units/mg.

What is claimed is:

1. A process for the purification of a crude, partially purified or contaminated, substantially non-crystalline nystatin which comprises:
   (i) forming an aqueous solution of nystatin by combining the nystatin starting material with water and an anionic surfactant;
   (ii) combining a chlorinated hydrocarbon solvent with the aqueous nystatin solution; and
   (iii) precipitating purified amorphous nystatin by adding an acid-addition salt of a mineral acid and a water-soluble amine.

2. A process in accordance with claim 1 wherein the anionic surfactant is sodium lauryl sulfate.

3. A process in accordance with claim 1 wherein the chlorinated hydrocarbon solvent is dichloromethane.

4. A process in accordance with claim 1 which further comprises filtering the aqueous nystatin solution prior to the addition of the chlorinated hydrocarbon solvent.

5. A process in accordance with claim 1 which further comprises converting the precipitated amorphous nystatin to a crystalline form.

6. A process in accordance with claim 1 which comprises:
   (i) combining the nystatin starting material with water and sodium lauryl sulfate;
   (ii) combining dichloromethane with the aqueous nystatin solution; and
   (iii) precipitating purified amorphous nystatin by adding an acid-addition salt of a mineral acid and a water-soluble amine.

* * * * *